(12) United States Patent
Nagahata et al.

(10) Patent No.: US 9,364,017 B2
(45) Date of Patent: Jun. 14, 2016

(54) INTESTINAL ENVIRONMENT-IMPROVING AGENT

(71) Applicant: J-OIL MILLS, INC., Tokyo (JP)

(72) Inventors: Yuya Nagahata, Tokyo (JP); Isao Kobayashi, Tokyo (JP); Masaru Goto, Tokyo (JP)

(73) Assignee: J-OIL MILLS, INC., Tokyo (JP)

( * ) Notice: Subject to any disclaimer, the term of this patent is extended or adjusted under 35 U.S.C. 154(b) by 0 days.

(21) Appl. No.: 14/395,743

(22) PCT Filed: Feb. 19, 2013

(86) PCT No.: PCT/JP2013/053983
§ 371 (c)(1),
(2) Date: Oct. 20, 2014

(87) PCT Pub. No.: WO2013/161359
PCT Pub. Date: Oct. 31, 2013

(65) Prior Publication Data
US 2015/0329648 A1 Nov. 19, 2015

(30) Foreign Application Priority Data

Apr. 26, 2012 (JP) ................................. 2012-100657

(51) Int. Cl.
| | | |
|---|---|---|
| *A01N 43/04* | (2006.01) | |
| *A61K 31/715* | (2006.01) | |
| *A23L 1/308* | (2006.01) | |
| *A23L 1/30* | (2006.01) | |
| *A23K 1/16* | (2006.01) | |
| *A23L 1/0522* | (2006.01) | |
| *A61K 31/717* | (2006.01) | |
| *A61K 31/718* | (2006.01) | |
| *C08B 31/00* | (2006.01) | |
| *A23L 2/52* | (2006.01) | |
| *A61K 31/716* | (2006.01) | |

(52) U.S. Cl.
CPC . *A23L 1/308* (2013.01); *A23K 1/16* (2013.01); *A23K 1/1643* (2013.01); *A23L 1/0522* (2013.01); *A23L 1/30* (2013.01); *A23L 2/52* (2013.01); *A61K 31/717* (2013.01); *A61K 31/718* (2013.01); *C08B 31/00* (2013.01); *A23V 2002/00* (2013.01); *A61K 31/715* (2013.01); *A61K 31/716* (2013.01)

(58) Field of Classification Search
None
See application file for complete search history.

(56) References Cited

U.S. PATENT DOCUMENTS

2012/0196023 A1    8/2012    Nagahata et al.

FOREIGN PATENT DOCUMENTS

| CN | 102018039 | 4/2011 |
|---|---|---|
| EP | 2183964 | 5/2010 |
| JP | 10-279487 | 10/1998 |
| JP | 2008-189625 | 8/2008 |
| JP | 2011-084674 | 4/2011 |
| WO | 2011/045902 | 4/2011 |

OTHER PUBLICATIONS

Thompson Trends in Food Science & Technology (2000), vol. 11, pp. 245-253.*
Li et al. Carbohydrate Polymers (2008), vol. 74, pp. 396-404.*
Freeman Cancer Research (1986), vol. 46, pp. 5529-5532.*
International Search Report dated May 21, 2013 filed in PCT/JP2013/053983.
Bird et al., "Two high-amylose maize starches with different amounts of resistant starch vary in their effects on fermentation, tissue and digesta mass accretion, and bacterial populations in the large bowel of pigs," British Journal of Nutrition, 2007, 97, pp. 134-144.
Brown et al., "Fecal Numbers of Bifidobacteria Are Higher in Pigs Fed bifidobacterium longum with a High Amylose Cornstarch Than with a Low Amylose Cornstarch," The Journal of Nutrition, 1997, 127, pp. 1822-1827.
Martinez et al., "Resistant Starches Types 2 and 4 Have Differential Effects on the Composition of the Fecal Microbiota in Human Subjects," Plos One, 2010, 5(11), e15046, pp. 1-11.
Park et al., "Resistant Starch Supplementation Influences Blood Lipid Concentrations and Glucose Control in Overweight Subjects," J Nutr sci Vitaminol, 2004, vol. 50, No. 2, pp. 93-99.
Nishimura et al., "Raw Chinese Yam (Dioscorea opposita) Promotes Cecal Fermentation and Reduces Plasma Non-HDL Cholesterol Concentration in Rats," J Nutr sci Vitaminol, 2011, vol. 57, No. 5, pp. 340-347.
Kleessen et al., "Feeding Resistant Starch Affects Fecal and Cecal Microflora and Short-Chain Fatty Acids in Rats," J. Anim. Sci., 1997, vol. 75, pp. 2453-2462.
Silvi et al., "Resistant Starch Modifies gut microflora and microbial metabolism in human flora-associated rats inoculated with faeces from Italian and U donors," Journal of Applied microbiology, 1999, vol. 86, pp. 521-530.
Chinese Office Action dated Dec. 30, 2015 issued in the corresponding Chinese patent application No. 201380021989.8.
European Search Report dated Mar. 17, 2016 issued in the corresponding European patent application No. 13781319.2.

* cited by examiner

*Primary Examiner* — Patrick Lewis
(74) *Attorney, Agent, or Firm* — Rankin, Hill & Clark LLP

(57) ABSTRACT

An intestinal environment-improving agent containing, as an effective component, a starch with a high resistant starch content that satisfies the following conditions (a), (b), (c), and (d):

(a) a content of a resistant starch measured by the resistant starch measurement method of AOAC official method 2002.02 is equal to or higher than 60%;

(b) a peak of a molecular weight is equal to or higher than $6 \times 10^3$ and equal to or lower than $4 \times 10^4$;

(c) a molecular weight dispersity is equal to or higher than 1.5 and equal to or higher than 6.0; and (d) a gelatinization enthalpy at 50° C. to 130° C. measured by a differential scanning calorimetry is equal to or lower than 10 J/g.

12 Claims, 6 Drawing Sheets

\* : THERE IS A SIGNIFICANT DIFFERENCE WITH RESPECT TO REFERENCE EXAMPLE 1. ($P<0.05$)
† : THERE IS A SIGNIFICANT DIFFERENCE WITH RESPECT TO REFERENCE EXAMPLE 1. ($P<0.01$)
‡ : THERE IS A SIGNIFICANT DIFFERENCE. ($P<0.05$)

SEQUENCE LISTING

```
<160> NUMBER OF SEQ ID NOS: 8

<210> SEQ ID NO 1
<211> LENGTH: 21
<212> TYPE: DNA
<213> ORGANISM: Artificial Sequence
<220> FEATURE:
<223> OTHER INFORMATION: Oligonucleotide to act as a PCR sense primer

<400> SEQUENCE: 1
actcctacgg gaggcagcag t                                          21

<210> SEQ ID NO 2
<211> LENGTH: 22
<212> TYPE: DNA
<213> ORGANISM: Artificial Sequence
<220> FEATURE:
<223> OTHER INFORMATION: Oligonucleotide to act as a PCR anti-sense
      primer

<400> SEQUENCE: 2
gtattaccgc ggctgctggc ac                                         22

<210> SEQ ID NO 3
<211> LENGTH: 20
<212> TYPE: DNA
<213> ORGANISM: Artificial Sequence
<220> FEATURE:
<223> OTHER INFORMATION: Oligonucleotide to act as a PCR sense primer

<400> SEQUENCE: 3
aaatgacggt acctgactaa                                            20

<210> SEQ ID NO 4
<211> LENGTH: 22
<212> TYPE: DNA
<213> ORGANISM: Artificial Sequence
<220> FEATURE:
```

```
<223> OTHER INFORMATION: Oligonucleotide to act as a PCR anti-sense
      primer

<400> SEQUENCE: 4
ctttgagttt cattcttgcg aa                                              22

<210> SEQ ID NO 5
<211> LENGTH: 20
<212> TYPE: DNA
<213> ORGANISM: Artificial Sequence
<220> FEATURE:
<223> OTHER INFORMATION: Oligonucleotide to act as a PCR sense primer

<400> SEQUENCE: 5
ggtgtcggct taagtgccat                                                 20

<210> SEQ ID NO 6
<211> LENGTH: 18
<212> TYPE: DNA
<213> ORGANISM: Artificial Sequence
<220> FEATURE:
<223> OTHER INFORMATION: Oligonucleotide to act as a PCR anti-sense
      primer

<400> SEQUENCE: 6
cggaygtaag ggccgtgc                                                   18

<210> SEQ ID NO 7
<211> LENGTH: 18
<212> TYPE: DNA
<213> ORGANISM: Artificial Sequence
<220> FEATURE:
<223> OTHER INFORMATION: Oligonucleotide to act as a PCR sense primer

<400> SEQUENCE: 7
tcgcgtcygg tgtgaaag                                                   18

<210> SEQ ID NO 8
<211> LENGTH: 17
<212> TYPE: DNA
<213> ORGANISM: Artificial Sequence
<220> FEATURE:
<223> OTHER INFORMATION: Oligonucleotide to act as a PCR anti-sense
      primer

<400> SEQUENCE: 8
ccacatccag crtccac                                                    17
```

INTESTINAL ENVIRONMENT-IMPROVING AGENT

TECHNICAL FIELD

The present invention relates to an intestinal environment-improving agent.

BACKGROUND ART

Generally, a starch is easily digested. However, the starch also includes an indigestible fraction, and such a fraction is called Resistant Starch (RS).

Non-Patent Document 1 describes that when a feed containing, as a resistant starch, a high-amylose corn starch or heat-moisture treated high-amylose corn starch is given to pigs, bifidobacteria numbers in feces increase.

Moreover, Non-Patent Document 2 describes that when a high-amylose corn starch and probiotic components are mixed with pig's feed, fecal numbers of bifidobacterial increase.

Furthermore, in Non-Patent Document 3, humans ingest the resistant starch so as to investigate changes in the bacteria. It is described that when a group ingests a wheat starch-containing food as a control group, a chemically modified starch of RS type 4 results in a significant difference in the increase in the number of bifidobacteria. On the contrary, it is described that a high-amylose corn starch of RS type 2 does not result in a significant difference in the number of bifidobacteria.

RELATED DOCUMENT

Patent Document

[Patent Document 1] Japanese Unexamined Patent Publication No. 2011-84674

Non-Patent Document

[Non-Patent Document 1] Anthony R. Bird et al., "Two high-amylose maize starches with different amounts of resistant starch vary in their effects on fermentation, tissue and digesta mass accretion, and bacterial populations in the large bowel of pigs", British journal of Nutrition, 2007, 97, 134-144

[Non-Patent Document 2] Ian Brown et al., "Fecal Numbers of Bifidobacteria Are Higher in Pigs Fed *Bifidobacterium longum* with a High Amylose Cornstarch Than with a Low Amylose Cornstarch", The Journal of Nutrition, 1997, 127, 1822-1827

[Non-Patent Document 3] Ines Martinez et al., "Resistant Starches Types 2 and 4 Have Differential Effects on the Composition of the Fecal Microbiota in Human Subjects", Plos one, 2010, 5 (11), e15046

DISCLOSURE OF THE INVENTION

Problems to be Solved by the Invention

As described above, reports on whether RS is effective for growth of Bifidobacteria is different for each researches, and the effectiveness of RS has not been clarified.

The present invention provides a novel intestinal environment-improving agent.

Means for Solving the Problems

According to the present invention, there is provided an intestinal environment-improving agent containing, as an effective component, a starch with a high resistant starch content that satisfies the following conditions (a), (b), (c), and (d).

(a) A content of a resistant starch measured by the resistant starch measurement method of AOAC official method 2002.02 is equal to or higher than 60%.

(b) A peak of molecular weight is equal to or higher than $6 \times 10^3$ and equal to or lower than $4 \times 10^4$.

(c) A molecular weight dispersity is equal to or higher than 1.5 and equal to or lower than 6.0.

(d) A gelatinization enthalpy at 50° C. to 130° C. measured by a differential scanning calorimetry is equal to or lower than 10 J/g.

Moreover, according to the present invention, there is provided a lipid metabolism-improving agent containing the intestinal environment-improving agent in the present invention.

Furthermore, according to the present invention, there is provided an intestinal environment-improving agent which contains, as an effective component, a starch with a high resistant starch content that satisfies the following conditions (a), (b), (c), and (d), and also contains an insoluble dietary fiber, and has a lipid metabolism-improving function.

(a) A content of a resistant starch measured by the resistant starch measurement method of AOAC official method 2002.02 is equal to or higher than 60%.

(b) A peak of molecular weight is equal to or higher than $6 \times 10^3$ and equal to or lower than $4 \times 10^4$.

(c) A molecular weight dispersity is equal to or higher than 1.5 and equal to or lower than 6.0.

(d) A gelatinization enthalpy at 50° C. to 130° C. measured by a differential scanning calorimetry is equal to or lower than 10 Jig.

In the present invention, containing the starch with a high resistant starch content that satisfies the conditions (a) to (d) as an effective component, so an excellent intestinal environment-improving effect can be obtained.

Moreover, even when the respective constituents of the present invention are combined in any way, or the form of the present invention is changed, according to the method, apparatus, and the like, they are also effective as embodiments of the present invention.

For example, according to the present invention, there is provided a medication, food or drink, or a feed containing the intestinal environment-improving agent in the present invention.

Furthermore, according to the present invention, there is provided a use of the intestinal environment-improving agent in the present invention to a medication, food or drink, or a feed.

Advantageous Effects of the Invention

According to the present invention, a novel intestinal environment-improving agent can be provided.

BRIEF DESCRIPTION OF THE DRAWING

The aforementioned object and other objects, characteristics, and advantages are further clarified by preferable embodiments described below and the following drawings accompanied by the embodiments.

DESCRIPTION OF EMBODIMENTS

Figure 1:
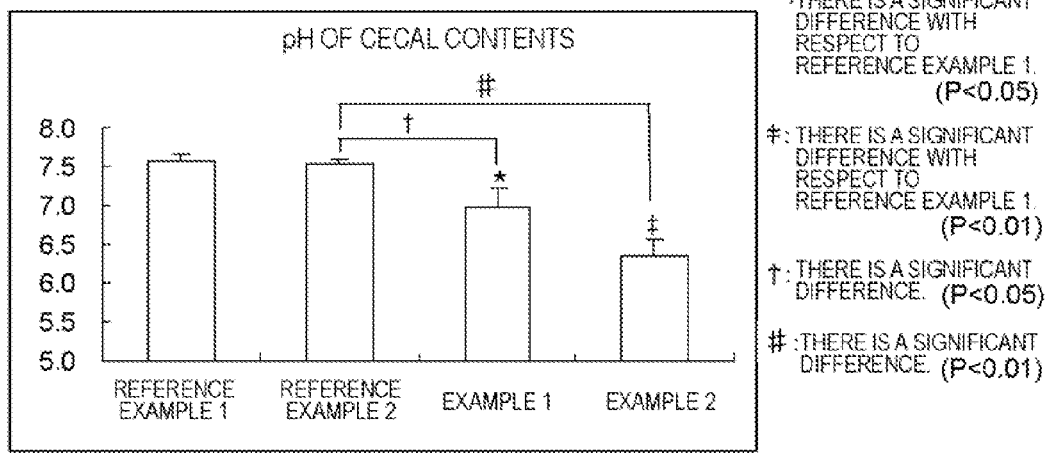
FIG. 1 A view showing measurement results of pH of cecal contents in examples.

The intestinal environment-improving agent of the present invention contains, as an effective component, a starch with a high resistant starch content that satisfies the following conditions (a), (b), (c), and (d).

(a) A content of a resistant starch measured by the resistant starch measurement method of AOAC official method 2002.02 is equal to or higher than 60%.

(b) A peak of molecular weight is equal to or higher than $6 \times 10^3$ and equal to or lower than $4 \times 10^4$.

(c) A molecular weight dispersity is equal to or higher than 1.5 and equal to or lower than 6.0.

(d) A gelatinization enthalpy at 50° C. to 130° C. measured by a differential scanning calorimetry is equal to or lower than 10 J/g.

First, starch with a high resistant starch content will be described.

Starch with a high resistant starch content used in the present invention satisfies the condition (a) and contains resistant starch in an amount markedly greater than that of the resistant starch contained in starch obtained by the production method that have been used so far.

From the viewpoint of further increasing an initial content of the resistant starch, the resistant starch content in the starch with a high resistant starch content in the present invention that is measured by the resistant starch measurement method of AOAC official method 2002.02 is preferably equal to or higher than 65% and more preferably equal to or higher than 70%. The upper limit of the resistant starch content in the starch with a high resistant starch content in the present invention is not limited. However, the upper limit is equal to or lower than 100%, and is, for example, equal to or lower than 90%.

Herein, the resistant starch content is defined as the resistant starch weight per a dry weight of a sample (w/w).

By satisfying the conditions (b) and (c), the resistant starch content in the starch can be stably increased.

Among the conditions, the condition (b) specifies a range of the molecular weight of the starch with a high resistant starch content.

By controlling the peak of a molecular weight to be equal to or higher than $6 \times 10^3$ and equal to or lower than $4 \times 10^4$, the starch in which the resistant starch content is higher than 60% is stably obtainable.

Form the viewpoint of more stably obtaining the starch with a high resistant starch content, the peak of molecular weight is, for example, equal to or higher than $6.5 \times 10^3$ and preferably equal to or higher than $8 \times 10^3$. Moreover, from the viewpoint of more reliably obtaining the starch with a high resistant starch content, the peak of a molecular weight may be, for example, equal to or lower than $3.6 \times 10^4$, preferably equal to or lower than $2.5 \times 10^4$, and more preferably equal to or lower than $1.5 \times 10^4$.

Next, the condition (c) specifies a molecular weight dispersity.

The molecular weight dispersity in the condition (c) refers to Mw/Mn which is a ratio of a weight average molecular weight Mw to a number average molecular weight Mn. By adopting the constitution of satisfying the condition (c), the resistant starch content can be stably increased, and it is possible to suppress an excessive increasing of the amount of a low-molecular weight fraction or a high-molecular weight fraction. Accordingly, it is possible to inhibit the intestinal environment-improving agent from becoming powdery to an excessive degree or to inhibit the eating texture of the agent from becoming hard to an excessive degree.

From the viewpoint of making the intestinal environment-improving agent have a good eating texture for ingestion, the lower limit of the molecular weight dispersity is equal to or higher than 1.5, preferably equal to or higher than 2.0, and more preferably equal to or higher than 3.0. Due to powderiness or the like, a starch with excessively low molecular weight dispersity has a poor eating texture in some cases. Accordingly, the peak of a molecular weight is preferably within a certain range.

Meanwhile, from the viewpoint of more stably increasing the resistant starch content, the upper limit of the molecular weight dispersity is equal to or lower than 6.0, preferably equal to or lower than 5.5, and more preferably equal to or lower than 5.0.

Therefore, from the viewpoint of balance between the proportion of the resistant starch and the eating texture, the molecular weight dispersity in the present invention is equal to or higher than 1.5 and equal to or lower than 6.0, preferably equal to or higher than 2.0 and equal to or lower than 5.5, and more preferably equal to or higher than 3.0 and equal to or lower than 5.0.

Moreover, the molecular weight of the starch may be measured by, for example, gel permeation chromatography (GPC) (standard substance: calculated as pullulan).

Next, the condition (d) will be described.

In the present invention, by satisfying the condition (d), it is possible to cause the intestinal environment-improving agent to contain the resistant starch at a high content as originally and also to make the resistant starch content be maintained at a high level even after a heating treatment is performed.

Specifically, it is possible to control the resistant starch content after heating for 20 minutes at 200° C. to be, for example, equal to or higher than 60% and preferably equal to or higher than 70%.

Herein, the gelatinization enthalpy is energy required for a starch to be gelatinized by heating. When the starch and water are heated together, the starch is gelatinized at a certain temperature. Since energy is required for the gelatinization, an endothermic reaction occurs. In Differential Scanning calorimetry (DSC), an endothermic energy amount associated with a temperature change is measured as a peak, and the peak area is calculated as the gelatinization enthalpy. The gelatinization enthalpy can be used as an index of a heat stability, for starches similar to each other in terms of the gelatinization temperature, the peak of a molecular weight, and the molecular weight dispersity.

One of the characteristics of the starch with a high resistant starch content of the present invention is that the area of an endothermic peak in DSC is small. Specifically, the gelatinization enthalpy is equal to or lower than 10 J/g, preferably equal to or lower than 8 J/g, and more preferably equal to or lower than 6 J/g. Thus, it is possible to stably obtain an intestinal environment-improving agent which contains a high amount of resistant starch even after cooking under heating. Furthermore, the lower limit of the gelatinization enthalpy is not limited and may be, for example, equal to or higher than 1 J/g.

In the present invention, the intestinal environment-improving agent contains, as an effective component, the starch with a high resistant starch content that satisfies all of the conditions (a) to (d). Accordingly, the agent contains resistant starch having an intestinal environment-improving function at a high proportion. Moreover, it is possible to obtain an intestinal environment-improving agent exhibiting an excellent stability during cooking under heating.

Next, a production method of the starch with a high resistant starch content will be described. In the present invention, the starch with a high resistant starch content may be produced according to the method described in, for example, Patent-Document 1.

Moreover, in the present specification, unless otherwise specified, the definition of each term is as follows. Furthermore, in the present specification, resistant starch is described as RS in some cases.

Slurry concentration: a ratio (w/w) of a dry starch weight to a starch slurry weight Acid normality: normality of an acid with respect to water in a reaction solution that includes a water content derived from starch (herein, the water content is a ratio (w/w) of a water content to a wet starch weight.)

Resistant starch content: a ratio (w/w) of a resistant starch weight to a dry sample weight Starch with a high resistant starch content: a starch in which a resistant starch content is equal to or higher than 60%

In the present invention, the starch with a high resistant starch content is obtainable by, for example, starch with a high amylose content having an amylose content of equal to or higher than 40% as a raw material and subjecting the raw material to an acid treatment in an aqueous inorganic acid solution.

The source of the starch with a high amylose content used as the raw material is not limited and includes corn, potato, rice, wheat, ocarina, tapioca, and the like. From the viewpoint of easy availability, a high-amylose corn starch is preferable. The high-amylose corn starch is a corn starch in which the amylose content is heightened by means of breeding. Currently, a high-amylose corn starch with the amylose content of equal to or higher than 40% or equal to or higher than 70% is available. From the viewpoint of more stably increasing the amount of the resistant starch contained in the starch with a high resistant starch content, any type of starch may be used as long as the amylose content in the starch is, for example, equal to or higher than 40%.

In the acid treatment, starch as a raw material and water were put into a reaction apparatus. Alternatively, acidic water, which is obtained by dissolving an inorganic acid in water, and a raw material were put into a reaction apparatus. From the viewpoint of more stably performing the acid treatment, it is desirable that during the reaction, the entirety of the starch be in a state of being uniformly dispersed in a water phase or in a state of being made into slurry. In order to create such a state, the concentration of the starch slurry at the time of the acid treatment is regulated to be, for example, equal to or lower than 50% by weight, and preferably within a range from equal to or higher than 20% by weight to equal to or lower than 40% by weight. When the slurry concentration is too high, viscosity of the slurry increases, and this makes it difficult to stir uniform slurry in some cases.

Specific examples of the acid used in the acid treatment include inorganic acids such as hydrochloric acid, sulfuric acid, and nitric acid, and these acids may be used regardless of the type, purity, and the like.

The acid treatment reaction is performed by appropriately selecting a temperature and an acid concentration suited for the obtained starch having undergone the acid treatment to satisfy the conditions (a) to (d). In the present invention, for example, the concentration of the inorganic acid, the reaction temperature, and the reaction time at the time of the acid treatment are set to specific conditions. Hereinafter, each of the conditions will be described in detail.

First, the time taken for the acid treatment is set such that the conditions (a) to (d) are satisfied. From the viewpoint of more reliably suppressing an alteration caused during the reaction, the time taken for the acid treatment is set to be, for example, within 3 days and preferably within 2 days.

Moreover, the concentration of the inorganic acid and the reaction temperature for the acid treatment is set to conditions such for example, the following Formula (1) is satisfied.

$$(5.54 \times (4.20)^{(T-40)/10})^{(-0.879)} \leq C \leq -0.000016 \times T^3 + 0.00068 \times T^2 - 0.028 \times T + 4.3 \quad (1)$$

(In the above Formula (1), T is a reaction temperature (° C.), C is normality (N) of an inorganic acid in an aqueous inorganic acid solution.)

When both the normality of the inorganic acid and the reaction temperature are too high, the resistant starch content may not be sufficiently increased in some cases. On the contrary, when they are too low, it takes too much time for the acid treatment reaction.

By setting the conditions satisfying the Formula (1), it is possible to efficiently and stably increase the resistant starch content.

Furthermore, the reaction time in the acid treatment may be specifically determined from two factors including the reaction temperature and the acid normality by the following Formula (2).

$$13.0 \times C^{(-1.14)} \times (1/4.2)^{(T-40)/10} \leq t \leq 180 \times C^{(-1.58)} \times (1/4.2)^{(T-40)/10} \quad (2)$$

(in the above Formula (2), T is a reaction temperature (° C.), C is normality (N) of an inorganic acid in an aqueous inorganic acid solution, and t is a reaction time (time).)

The Formula (2) is an experimentally obtained formula and is based on a relationship in which when the acid normality is doubled, a minimum time and a maximum time required for obtaining the starch with a high resistant starch content is decreased by 1/2.2-fold and ⅓-fold respectively, and when the reaction temperature is increased by 10° C., both the minimum time and maximum time is decreased by 1/4.2-fold.

The production conditions of the starch with a high resistant starch content are represented by three factors including the reaction temperature, the acid normality, and the reaction time. Moreover, the upper limit and lower limit of the reaction temperature and the acid normality used in Formula (2) are determined by the Formula (1) described above.

When the starch with a high amylose content (high-amylose starch) having an amylose content of equal to or higher than 40% is used as a raw material, and the raw material is subjected to the acid treatment in the aqueous inorganic acid solution under specific conditions, the starch with a high resistant starch content is stably obtainable.

Furthermore, when the starch with a high amylose content having an amylose content of equal to or higher than 40% is used as a raw material and subjected to the acid treatment, and the reaction temperature, the acid normality, and the reaction time at the time of the acid treatment are set to specific conditions respectively, the resistant starch content can be greatly increased. Moreover, the absolute amount of resistant starch in the high-amylose starch can be increased with a high efficiency.

The starch with a high resistant starch content obtainable as above contains the resistant starch in a high proportion, excellent in heating stability of the resistant starch, and is effective as an intestinal environment-improving agent.

Hereinafter, the intestinal environment-improving agent will be described in more detail.

First Embodiment

The intestinal environment-improving agent in the present embodiment contains, as an effective component, starch with a high resistant starch content that satisfies the aforementioned conditions (a), (b), (c), and (d).

The intestinal environment-improving agent in the present embodiment has a function of increasing the number of an enteric bacteria belonging to the genus *Bifidobacterium*.

The content of the starch with a high resistant starch content in the intestinal environment-improving agent is not limited. From the viewpoint of efficiently increasing the number of the enteric bacteria belonging to the genus *Bifidobacterium*, the content is, for example, equal to or higher than 5% by weight, preferably equal to or higher than 10% by weight, and more preferably equal to or higher than 15% by weight. Furthermore, the content of the starch with a high resistant starch content in the intestinal environment-improving agent is not limited, and is equal to or lower than 100% by weight. The content may be set according to the form of the agent.

The form of the intestinal environment-improving agent is not limited, and the agent may be formed into, for example, a capsule, a tablet, granules, fine granules, and powder.

Moreover, the intestinal environment-improving agent may be used as is as a medication, a quasi-drug, a food additive, drink or food, a feed, and the like. In addition, the agent may be used by being mixed in these in a certain proportion.

The amount of the intestinal environment-improving agent mixed in is not limited. When it is mixed in a drink or food, or a feed, from the viewpoint of making the agent efficiently function to increase the number of bacteria belonging to the genus *Bifidobacterium*, the amount may be controlled to be, for example, equal to or greater than 1% by weight. The amount is preferably controlled to be equal to or greater than 3% by weight, and more preferably controlled to be equal to or greater than 5% by weight. Furthermore, from the viewpoint of inhibiting deterioration of the flavor or eating texture unique to the drink or food, or the feed, the amount of the intestinal environment-improving agent mixed in is controlled to be, for example, equal to or less than 50% by weight, preferably equal to or less than 30% by weight, and more preferably equal to or less than 20% by weight.

The dosage of the intestinal environment-improving agent may be set according to, for example, the content of the effective component of the intestinal environment-improving agent, an age of a patient, the medical condition or normal condition of the patient, and a method of administration. From the viewpoint of more reliably obtaining the function of increasing the number of bacteria belonging to the genus *Bifidobacterium*, the dosage for adults may be set such that the effective component is administered in an amount of, for example, equal to or greater than 50 mg and preferably equal to or greater than 100 mg a day per 1 kg of body weight.

Moreover, the upper limit of the dosage of the intestinal environment-improving agent is not limited, and for adults, the dosage may be set such that the effective component is administered in an amount of, for example, equal to or less than 5 g a day per 1 kg of body weight.

In addition, according to the intestinal environment-improving agent of the present embodiment, it is possible to obtain, for example, a function of increasing the amount of an organic acid or decreasing intestinal pH while maintaining food intake or growth in a normal state.

Moreover, according to the intestinal environment-improving agent in the present embodiment, it is possible to obtain a function of increasing a weight of feces; a function of increasing a weight of intestine; and one, two, or more functions selected from a group consisting of a function of decreasing a total cholesterol level in blood, a function of decreasing triglyceride levels in blood, and a lipid metabolism-improving function such as a function of decreasing an arteriosclerotic index represented by the following Formula (I).

$$\text{Arteriosclerotic index} = ((\text{total cholesterol concentration (mg/dl)}) - (\text{HDL cholesterol concentration (mg/dl)}))/(\text{HDL cholesterol concentration (mg/dl)}) \quad (I)$$

Second Embodiment

The intestinal environment-improving agent in the present embodiment contains, as an effective component, the starch with a high resistant starch content that satisfies the aforementioned conditions (a), (b), (c), and (d). More specifically, the intestinal environment-improving agent in the present embodiment contains, as an effective component, the starch with a high resistant starch content that satisfies the conditions (a), (b), (c), and (d) and also contains insoluble dietary fiber other than the starch with a high resistant starch content.

The intestinal environment-improving agent in the present embodiment has a lipid metabolism-improving function. Examples of the lipid metabolism-improving function include one, two, or more functions selected from a group consisting of a function of decreasing a total cholesterol level in blood, a function of decreasing triglyceride levels in blood, and a function of decreasing an arteriosclerotic index represented by the following Formula (I).

$$\text{Arteriosclerotic index} = ((\text{total cholesterol concentration (mg/dl)}) - (\text{HDL cholesterol concentration (mg/dl)}))/(\text{HDL cholesterol concentration (mg/dl)}) \quad (I)$$

Moreover, in the present embodiment, the starch with a high resistant starch content and the insoluble dietary fiber are used in combination. Consequentially, a synergistic effect is obtainable, whereby the lipid metabolism-improving function can be markedly improved.

Dietary fiber is classified into an insoluble dietary fiber, a water-soluble dietary fiber, an indigestible oligosaccharide, and a resistant starch.

Examples of the insoluble dietary fiber include one, two, or more kinds selected from a group consisting of cellulose, hemicelluloses, lignin, chitosan, chitin, and cellulose derivatives such as carboxymethyl cellulose and hydroxypropyl cellulose. Among these, cellulose is a main component constituting the cell wall of plants and yeasts and is a typical compound of insoluble dietary fiber that is easy to use. The source of the insoluble dietary fiber is not limited, and it is possible to use insoluble dietary fiber derived from plants, animals, fungi and the like.

In the present embodiment, one kind of the insoluble dietary fiber may be mixed in the intestinal environment-improving agent, or two or more kinds thereof may be mixed in the agent in combination.

The content of the starch with a high resistant starch content and the insoluble dietary fiber in the intestinal environment-improving agent are not limited. From the viewpoint of efficiently improving lipid metabolism, the content of the starch with a high resistant starch content in the intestinal environment-improving agent is, for example, equal to or higher than 5% by weight, preferably equal to or higher than 10% by weight, and more preferably equal to or higher than 15% by weight. Furthermore, the content of the starch with a high resistant starch content in the intestinal environment-improving agent is not limited and is equal to or less than 100% by weight. The content may be set according to the form of the agent.

Moreover, in the present embodiment, the type of the insoluble dietary fiber is not limited. From the viewpoint of easy availability, for example, one or more kinds or two kinds selected from among cellulose and derivatives thereof may be used, and among these, cellulose is preferably used.

The amount of the insoluble dietary fiber mixed in the intestinal environment-improving agent may be set as appropriate within a range in which the effect of the starch with a high resistant starch content is sufficiently obtainable. For example, the amount may be set to be equal to or greater than 5% by weight.

Furthermore, in the present invention, the starch with a high resistant starch content and the insoluble dietary fiber are used in combination. Consequentially, a synergistic effect is obtainable, whereby the lipid metabolism-improving function can be markedly improved.

For example, the amount of the starch with a high resistant starch content mixed in the intestinal environment-improving agent may be controlled to be equal to or greater than 5% by weight and equal to or less than 95% by weight, and the amount of the insoluble dietary fiber mixed in the agent may be controlled to be equal to or greater than 5% by weight and equal to or less than 95% by weight. The amount of the starch with a high resistant starch content mixed in the agent is preferably controlled to be equal to or greater than 10% by weight and equal to or less than 90% by weight, and the amount of the insoluble dietary fiber mixed in the agent is preferably controlled to be equal to or greater than 10% by weight and equal to or less than 90% by weight.

The form of the intestinal environment-improving agent is not limited, and the agent may be formed into, for example, a capsule, a tablet, granules, fine granules, and powder.

Moreover, the intestinal environment-improving agent may be used as is as a medication, a quasi-drug, a food additive, drink or food, a feed, and the like. In addition, the agent may be used by being mixed in these in a certain proportion.

The amount of the intestinal environment-improving agent mixed in is not limited. However, when it is mixed in a drink or food, or a feed, from the viewpoint of making the agent efficiently function to improve lipid metabolism, the amount may be controlled to be, for example, equal to or greater than 1% by weight. The amount is preferably controlled to be equal to or greater than 3% by weight, and more preferably controlled to be equal to or greater than 5% by weight. Furthermore, from the viewpoint of inhibiting deterioration of the flavor or eating texture unique to the drink or food, or the feed, the amount of the intestinal environment-improving agent mixed in is controlled to be, for example, equal to or less than 50% by weight, preferably equal to or less than 30% by weight, and more preferably equal to or less than 20% by weight.

In addition, a mixing ratio between the starch with a high resistant starch content and the insoluble dietary fiber is, for example, about 5:95 to 95:5, preferably about 20:80 to 80:20, and more preferably about 30:70 to 70:30.

The dosage of the intestinal environment-improving agent may be set according to, for example, the content of the effective component of the intestinal environment-improving agent, an age of the patient, the medical condition or normal condition of the patient, and a method of administration. From the viewpoint of more reliably obtaining the lipid metabolism-improving function, the dosage for adults may be set such that the effective component is administered in an amount of, for example, equal to or greater than 50 mg and preferably equal to or greater than 100 mg a day per 1 kg of body weight.

Moreover, the upper limit of the dosage of the intestinal environment-improving agent is not limited, and for adults, the dosage may be set such that the effective component is administered in an amount of, for example, equal to or less than 5 g a day per 1 kg of body weight.

In addition, according to the intestinal environment-improving agent of the present embodiment, it is possible to obtain, for example, a function of increasing the amount of an organic acid or decreasing intestinal pH while maintaining food intake or growth in a normal state.

Moreover, according to the intestinal environment-improving agent in the present embodiment, it is possible to obtain a function of increasing a weight of feces, a function of increasing a weight of intestine, and the like.

EXAMPLES

Hereinafter, examples of the present invention will be described, but the gist of the present invention is not limited to the examples.

Furthermore, in the following description, unless otherwise specified, "%" means "% by weight".

Production Example

Production of a Starch with a High Resistant Starch Content

Based on the method described in Patent Document 1, a starch with a high resistant starch content that satisfies the aforementioned conditions (a) to (d) was produced.

Specifically, high-amylose corn starch HS-7 class VII (manufactured by J-OIL MILLS, INC., water content of 15.0%, amylose content of 80%) was used, and water was added thereto such that a dry starch weight with respect to a slurry weight (dry starch weight/slurry weight) became 40%, thereby preparing 320 g of slurry. Thereafter, 80 mL of a 2.06 N aqueous hydrochloric acid solution was added thereto in a state of suspending the slurry, and the resultant was heated to 50° C. At this time, the normality of the hydrochloric acid in reaction water including water content of the starch was 0.61 N. After the reaction was performed for 24 hours, the resultant was neutralized with 3% NaOH, washed with water, dehydrated, and dried, thereby obtaining acid-treated high-amylose corn starch (the starch with a high resistant starch content). Herein, the acid normality refers to an acid normality in reaction water including the water content of the starch in the finally obtained reaction solution.

The obtained starch with a high resistant starch content had: a resistant starch content of 70.8% (measured by the measurement method according to AOAC official method 2002. 02);
a peak of a molecular weight of 8,500;
a molecular weight dispersity of 4.2; and
a gelatinization enthalpy measured by DSC of 4.0 J/g. Herein, each of the molecular weight distribution and gelatinization enthalpy was measured by the following method.

(Measurement of Molecular Weight Distribution)

The molecular weight distribution (a peak of a molecular weight and a molecular weight dispersity) were measured using HPLC unit (including DP-8020 as a pump, RS-8021 as an IR detector, and SD-8022 as a deaerator) manufactured by TOSOH CORPORATION. The analysis conditions are as follows.
Column: two TSKgel α-M (7.8 mmϕ, 30 cm) columns (manufactured by TOSOH CORPORATION)
Flow rate: 0.5 ml/min
Mobile phase: 5 mM $NaNO_3$/dimethylsulfoxide:water (9:1)
Column temperature: 40° C.
Analyzed amount: 0.2 mL (a sample concentration is 1.0 mg per 1 mL of a mobile phase)

Data of the detector was collected using dedicated software (Multistation GPC-8020 model II data collection version 5.70, manufactured by TOSOH CORPORATION), and the peak molecular weight and the molecular weight dispersity were calculated. A calibration curve was prepared using pullulan (manufactured by SHOWA DENKO K.K., Shodex Standard P-82) of which the molecular weight had already been known.

(Measurement of Gelatinization Enthalpy by Differential Scanning Calorimetry (DSC))

For a DSC measurement, DSC3100 manufactured by MAC Science Co., Ltd. was used. 15 mg of the sample and 45 μL of distilled water were put in an aluminum cell having a volume of 70 μL the cell was covered with a lid and sealed, and left at room temperature for 3 hours or longer such that the cell absorbed the water. As a reference, a blank cell was used. The cell was heated to 130° C. from room temperature at a rate of 10° C./min. The gelatinization enthalpy as an energy measured from the area of an endothermic peak of the obtained DSC chart was defined as energy to gelatinize starch per dry starch weight (J/g).

Examples 1 and 2 and Reference Examples 1 and 2

An administration test was performed using rats. In Example 1, a feed containing an intestinal environment-improving agent composed of the starch with a high resistant starch content obtained in the preparation example and a cellulose was administered to the rats. In Example 2, a feed containing an intestinal environment-improving agent composed of the starch with a high resistant starch content obtained in the production example was administered to the rats.

Each of the test feed, test condition, test method, and test result is as follows.

(Test Feed)

A feed as a high-fat, high-cholesterol and high-sucrose diet was prepared by mixing the components together as shown in Table 1. In each example, the following high-fat, high-cholesterol and high-sucrose diet was used.
Reference Example 1: starch diet (10% of a corn starch)
Reference Example 2: cellulose diet (10% of a cellulose)
Example 1: 5% RS diet (5% of the starch with a high resistant starch content, 5% of a cellulose)
Example 2: 10% RS diet (10% of the starch with a high resistant starch content)

TABLE 1

Composition of feed (high-fat, high-cholesterol and high-sucrose diet)

|  | Reference Example 1 (starch) | Reference Example 2 (cellulose) | Example 1 (5% RS) | Example 2 (10% RS) |
|---|---|---|---|---|
| Milk casein (%) | 25.000 | 25.000 | 25.000 | 25.000 |
| Pregelatinized starch (%) | 9.869 | 9.869 | 9.869 | 9.869 |
| Corn starch(%) | 10.000 | — | — | — |
| Starch with a high resistant starch content (%) | — | — | 5.000 | 10.000 |
| Cellulose powder (%) | — | 10.000 | 5.000 | — |
| Sucrose (%) | 20.000 | 20.000 | 20.000 | 20.000 |
| Beef tallow (%) | 14.000 | 14.000 | 14.000 | 14.000 |
| Lard (%) | 14.000 | 14.000 | 14.000 | 14.000 |
| Soybean oil (%) | 2.000 | 2.000 | 2.000 | 2.000 |
| AIN-93 vitamin mix (%) | 1.000 | 1.000 | 1.000 | 1.000 |
| AIN-93G mineral mix (%) | 3.500 | 3.500 | 3.500 | 3.500 |
| Choline bitartrate (%) | 0.250 | 0.250 | 0.250 | 0.250 |
| L-cystine (%) | 0.375 | 0.375 | 0.375 | 0.375 |
| tert-Butylhydroquinone (%) | 0.006 | 0.006 | 0.006 | 0.006 |
| Total (%) | 100.000 | 100.000 | 100.000 | 100.000 |
| Kcal/100 g | 501 | 461 | 476 | 491 |

The components used in Table 1 are as follows.
Corn starch: Regular corn starch (manufactured by J-OIL MILLS, INC.) Starch with a high resistant starch content: the starch with a high resistant starch content obtained in the production example
Cellulose powder: a crystalline cellulose (manufactured by CLEA Japan, Inc.)

(Test Conditions)

Twenty eight of 7-week-old male blister rats were adapted for 5 days being fed with a normal feed. Thereafter, based on the body weight and blood biochemistry, the rats were divided into four groups (7 rats per group) and fed with the feed (Table 1) of each example for 5 weeks.

During the test period, the body weight was measured once a week, and the food intake was measured twice a week. Feces during 24 hours was collected at the end of the test period and the rats were fasted for 4 hours. Subsequently, the rats were anesthetized with diethyl ether, and blood was collected from their inferior vena cava. Next, the liver, the cecum, and epididymal white tissue were collected from the rats. Moreover, the cecal contents were collected, and pH of the cecal contents was measured.

(Test Method)

(pH of Cecal Contents)

50 mg of the cecal contents were suspended in 1 mL of water, and pH thereof was measured using a pH meter.

(Short-Chain Fatty Acids in Cecum)

95% ethanol, which was in an amount 5 times of the amount of the cecal contents, was added to 0.5 g of the cecal contents for extracting fatty acids. Thereafter, by using a YMC fatty acid analysis kit (manufactured by YMC CO., LTD.), the fatty acids were labeled, and HPLC was performed under the following conditions.
Analysis column: YMC-pack FA (250×6.0 mm ID) (manufactured by YMC CO., LTD.)
Mobile phase: acetonitrile/methanol/water (30/16/54), pH of which was set to be 4.5 by using 0.1 N hydrochloric acid
Flow rate: 1.2 mL/min
Column temperature: 40° C.
Detection: absorption of DV at 400 nm (Analysis of Microflora in Cecal Contents)

Two specimens were randomly selected from the respective groups, and DNA was extracted from the cecal contents by using a DNA extraction kit (QIUAmp DNA stool Mini Kit, manufactured by QIAGEN). The number of the respective bacteria was measured using a real time PCR apparatus Line-Gene (manufactured by BioFlux), and a relative value of the respective bacteria was calculated using a comparative ct method based on the value of the group supplemented with starch.

The determination methods for the respective bacteria are as follows.

For measuring a total bacterial count, PCR was performed using 0.04 µg of DNA as a template, a sense primer (SEQ ID NO. 1:5'-actcctacgggaggcagcagt-3'), and an antisense primer (SEQ ID NO. 2: 5'-gtattaccgcggctgctggcac-3'). The reaction was performed in 20 µL of a PCR solution by using 10 µL of SYBR® Premix Ex Taq™ (Perfect Real Time) (manufactured by TAKARA BIO INC.) and 0.4 µM of the respective primers under the following PCR program.
1 Cycle: 95° C., 10 sec; 40 cycles: 95° C., 20 sec, 61° C., 31 sec; 1 cycle (dissociation): 95° C., 15 sec, 60° C., 30 sec, 95° C., 15 sec The total bacterial count was calculated as a relative value determined when the value of the group supplemented with starch was regarded as being 1.

A *Clostridium-coccoides* group was subjected to PCR by using 0.02 µg of DNA as a template, a sense primer (SEQ ID NO. 3:5'-aaatgacggtacctgactaa-3'), and an antisense primer (SEQ ID NO. 4: 5'-ctttgagtttcattcttgcgaa-3'). The reaction was performed in 20 µL of a PCR solution by using 10 µL of SYBR® Premix Ex Taq™ (Perfect Real Time) (manufactured by TAKARA BIO INC.) and 0.4 µM of the respective primers under the following PCR program.
1 Cycle: 95° C., 10 sec; 40 cycles: 94° C., 20 sec, 58° C., 20 sec, 72° C., 30 sec; 1 cycle (dissociation): 95° C., 15 sec, 60° C., 30 sec, 95° C., 15 sec The value of the *Clostridium-coccoides* group was calculated as a relative value determined when the value of the group supplemented with starch was regarded as being 1.

A *Bacteroides-Prevotella* group was subjected to PCR by using 0.02 µg of DNA as a template, a sense primer (SEQ ID NO. 5:5'-ggtgtcggcttaagtgccat-3'), and an antisense primer (SEQ ID NO. 6: 5'-cggavgtaagggccgtgc-3'). The reaction was performed in 20 µL of a PCR solution by using 10 µL of SYBR® Premix Ex Taq™ (Perfect Real Time) (manufactured by TAKARA BIO INC.) and 0.4 µM of the respective primers under the following PCR program.
1 Cycle: 95° C., 10 sec; 40 cycles: 95° C., 20 sec, 58° C., 10 sec, 72° C., 30 sec; 1 cycle (dissociation): 95° C., 15 sec, 60° C., 30 sec, 95° C., 15 sec The value of the *Bacteroides-Prevotella* group was calculated as a relative value determined when the value of the group supplemented with starch was regarded as being 1.

*Bifidobacterium* was subjected to PCR by using 0.01 µg of DNA as a template, a sense primer (SEQ ID NO. 7:5'-tcgcgt-cyggtgtgaaag-3'), and an antisense primer (SEQ ID NO. 8: 5'-ccacatccagcrtccac-3'). The reaction was performed in 20 µL of a PCR solution by using 10 µL of SYBR® Premix Ex Taq™ (Perfect Real Time) (manufactured by TAKARA BIO INC.) and 0.4 µM of the respective primers under the following PCR program.
1 Cycle: 95° C., 10 sec; 40 cycles: 95° C., 20 sec, 62° C., 20 sec, 72° C., 30 sec; 1 cycle (dissociation): 95° C., 15 sec, 60° C., 30 sec, 95° C., 15 sec The value of the *Bifidobacterium* was calculated as a relative value determine d when the value of the group supplemented with starch was regarded as being 1.

(Weight of Feces)

Feces that the rats produced for 24 hours at the end of the test period were collected and freeze-dried. Thereafter, a dry weight of the obtained feces was measured.

(Amount of Cecum)

From the excised cecum, cecal contents were collected. Moreover, after the inside of the cecum was washed, a weight of the cecum was measured.

(Analysis of Lipid in Blood)

The lipid in blood was analyzed using a lipoprotein analysis system LipoSEARCH (Skylight Biotech, Inc.).

(Statistical Analysis)

Statistical data processing was performed using StatView 5.0, and for a multiple comparison test, Fisher's PLSD was used.

(Test Result)

(pH of Cecal Contents)

FIG. 1 is a view showing measurement results of pH of the cecal contents. From FIG. 1, it was confirmed that the level of pH of the cecal contents is markedly lower in Examples 1 and 2 supplemented with the starch with a high resistant starch content, than in Reference Example 1 (the group supplemented with starch) and Reference Example 2 (the group supplemented with cellulose), and there is a significant difference in the level of pH between Reference Examples 1 and 2 and Examples 1 and 2.

(Short-Chain Fatty Acids in Cecum)

Figure 2:
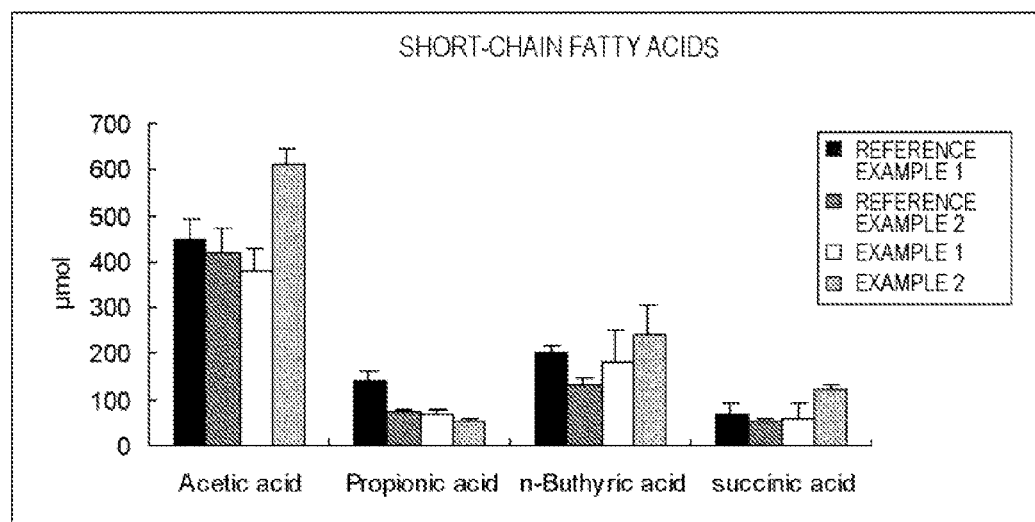
FIG. 2 A view showing measurement results of short-chain fatty acids in cecal contents in examples.

FIG. 2 is a view showing measurement results of organic acids (short-chain fatty acids) in the cecal contents.

As shown in FIG. 2, the amount of the short-chain fatty acids in the cecal contents was markedly great in Example 2 for any of the acetic acid, butyric acid, and succinic acid.

(Analysis of Microflora in Cecal Contents)

FIGS. 3 to 6 are views showing analysis results of microflora in the cecal contents.

Figure 3:
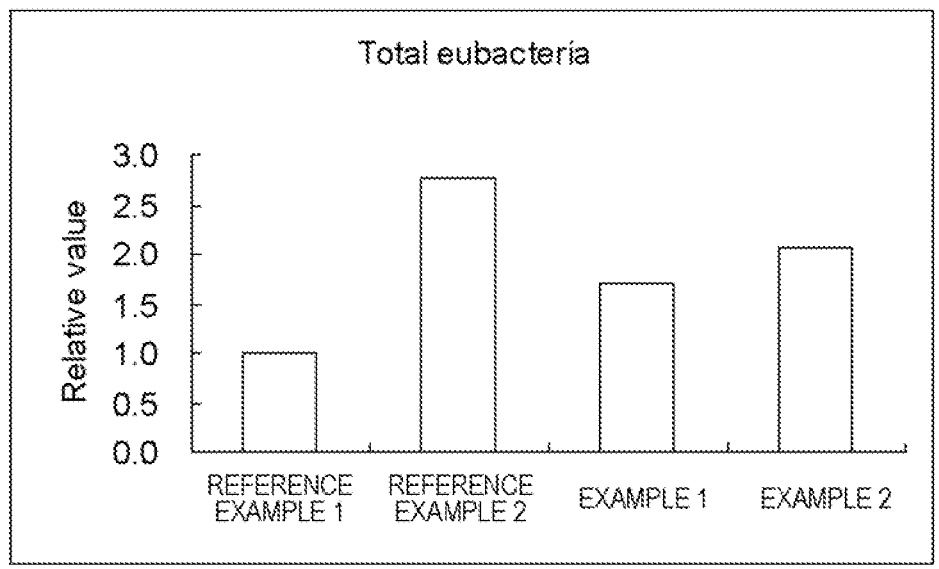
FIG. 3 A view showing analysis results of microflora in cecal contents in examples.

As shown in FIG. 3, the total bacterial count in the cecal contents was markedly higher in Reference Example 2 than in Reference Example 1. The total bacterial count was also high in Examples 1 and 2.

Figure 4:
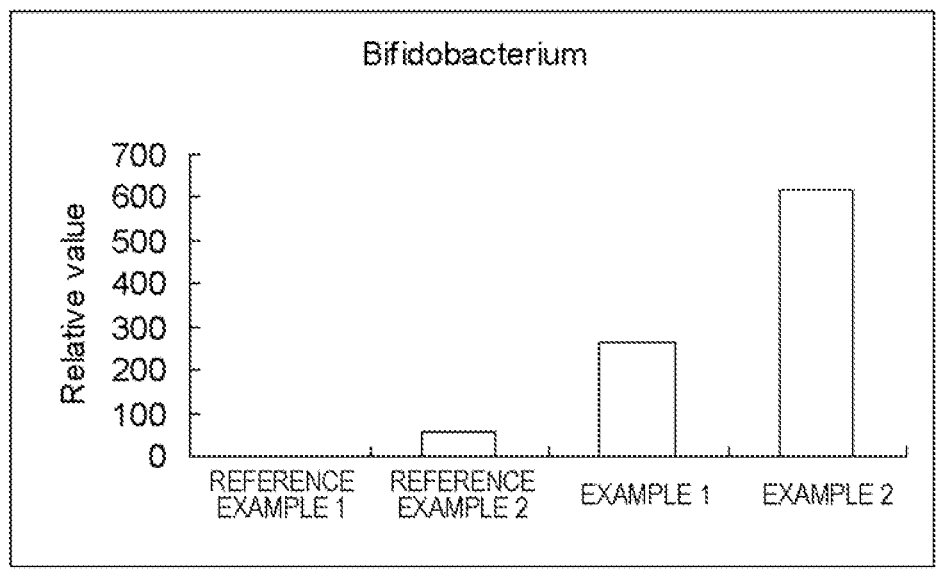
FIG. 4 A view showing analysis results of microflora in cecal contents in examples.

As shown in FIG. 4, in Reference Example 2, the number of *Bifidobacterium* in the cecal contents was increased and became about 56 times of the number of the bacteria in Reference Example 1. It was additionally increased and became 270 times in Example 1, and 620 times in Example 2.

Figure 5:
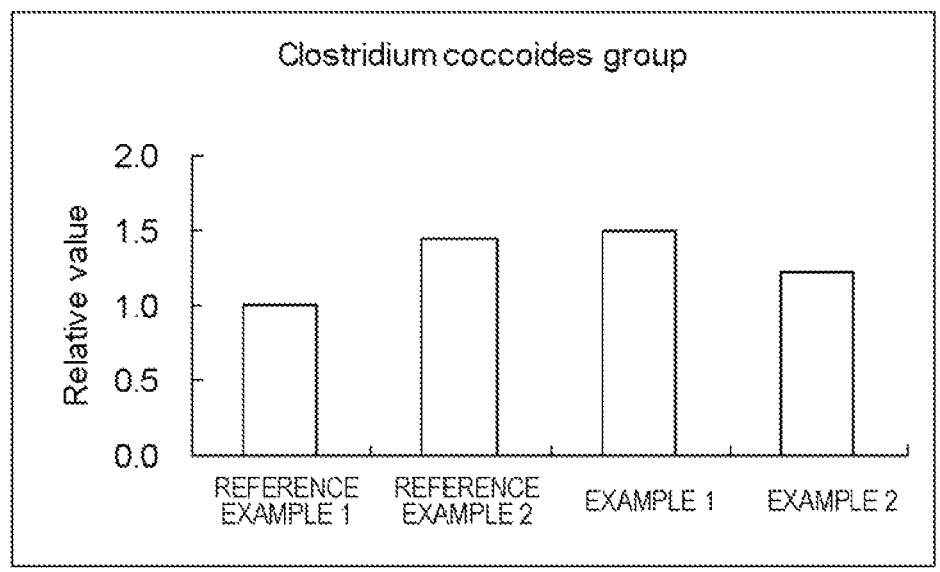
FIG. 5 A view showing analysis results of microflora in cecal contents in examples.

As shown in FIG. 5, regarding the *Clostridium cocoides* group in the cecal contents, a marked difference was not observed between the respective examples.

Figure 6:
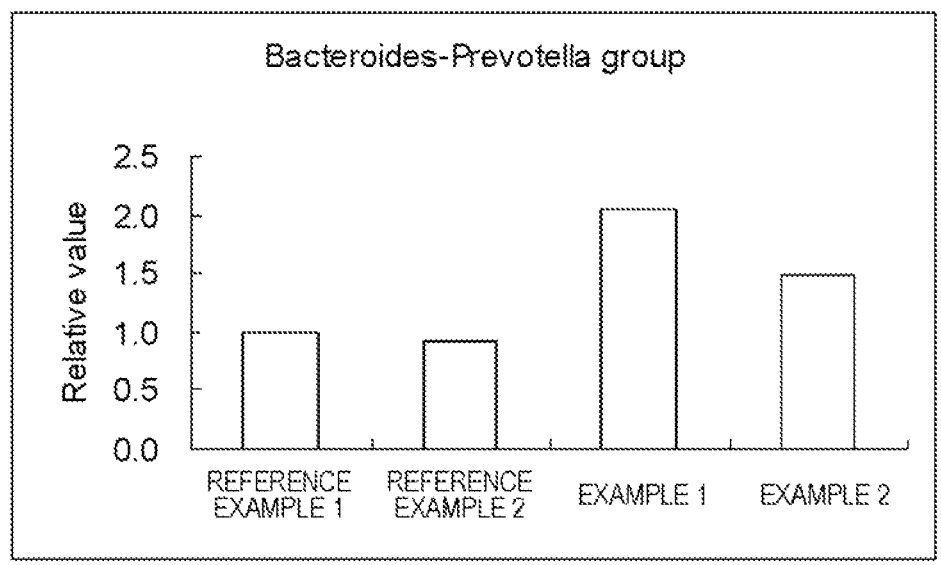
FIG. 6 A view showing analysis results of microflora in cecal contents in examples.

As shown in FIG. 6, regarding the *Bacteroides-Prevotella* group in the cecal contents, a marked difference was not observed between the respective examples.

(Weight of Feces)

Figure 7:
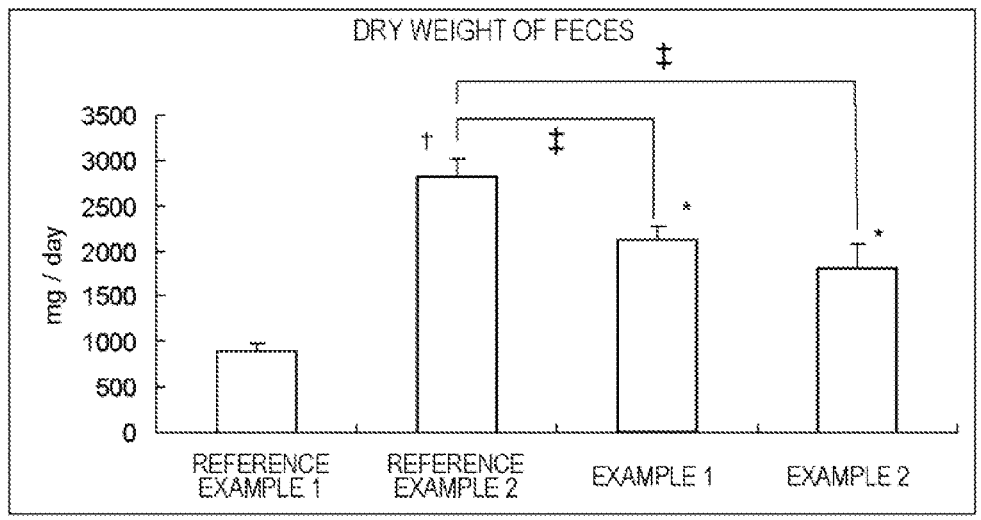
FIG. 7 A view showing measurement results of a dry weigh of feces in examples.

FIG. 7 is a view showing measurement results of a dry weight of feces. As shown in FIG. 7, the weight of feces produced per day was significantly higher in Reference Example 2 and Examples 1 and 2 than in Reference Example 1.

(Amount of Cecum)

Figure 8:
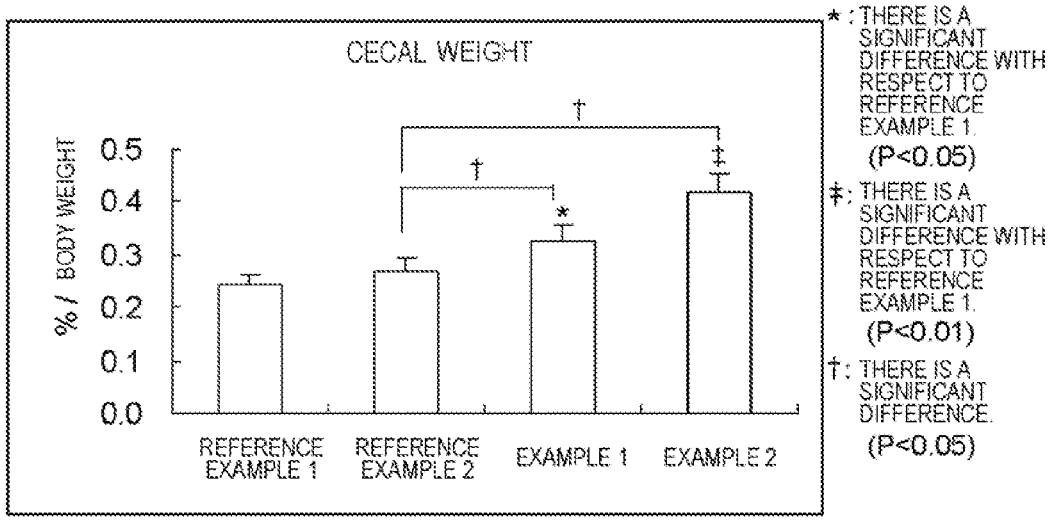
FIG. 8 A view showing measurement results of a weight of cecum in examples.

FIG. 8 is a view showing measurement results of an weight of cecum. As shown in FIG. 8, the weight of cecum was markedly higher in Examples 1 and 2 than in Reference Example 1, and a significant difference was observed between the examples. The weight of cecum of Examples 1 and 2 was also significantly higher, compared to Reference Example 2.

(Analysis of Lipid in Blood)

Figure 9:
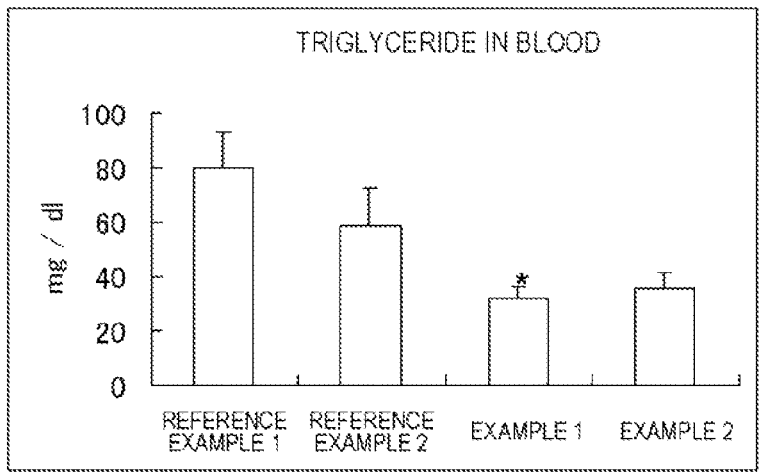
FIG. 9 A view showing measurement results of a triglyceride level in blood in examples.

FIG. 9 is a view showing measurement results of a triglyceride level in blood. As shown in FIG. 9, the level of triglyceride in blood was markedly lower in Examples 1 and 2 than in Reference Examples 1 and 2. Furthermore, a significant difference was observed between Example 1 and Reference Example 1.

Figure 10:
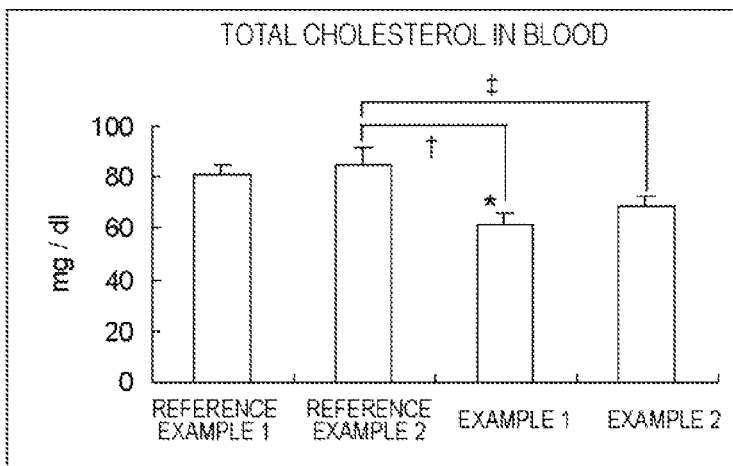
FIG. 10 A view showing measurement results of the total cholesterol level in blood in examples.

FIG. 10 is a view showing measurement results of the total cholesterol level in blood. As shown in FIG. 10, regarding the total cholesterol level in blood, a significant difference was observed between Reference Example 1 and Example 1, and between Reference Example 2 and Examples 1 and 2.

Table 2 shows measurement results of cholesterol balance. In Table 2, an arteriosclerotic index was calculated by the aforementioned Formula (1). From Table 2, the groups having ingested the starch with a high resistant starch content of Examples 1 and 2 exhibit the improvement of the cholesterol balance.

TABLE 2

| | Reference Example 1 | Reference Example 2 | Example 1 | Example 2 |
|---|---|---|---|---|
| Arteriosclerotic index | 0.67 | 0.65 | 0.58 | 0.55 |

(Total Food Intake)

Figure 11:
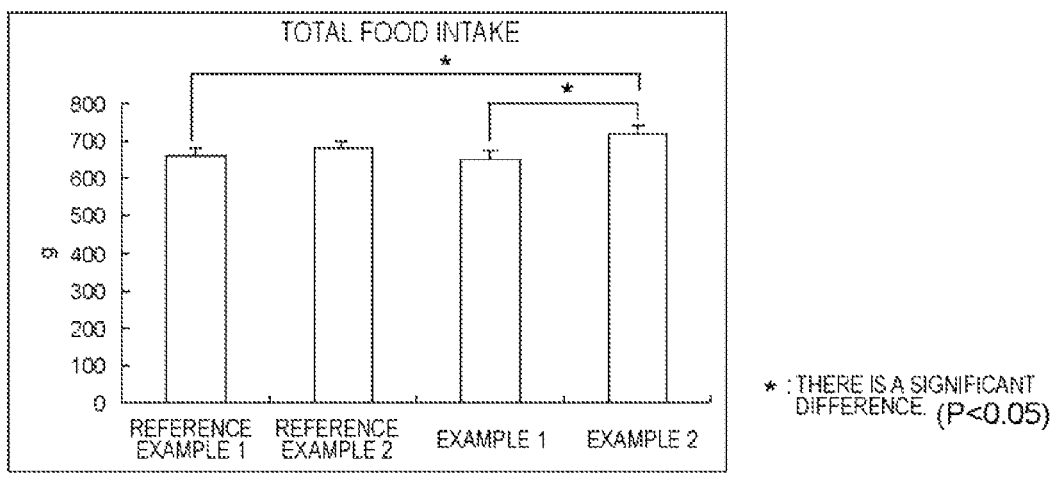
FIG. 11 A view showing a total food intake during a test period in examples.

FIG. 11 is a view showing a total food intake during the test period. As shown in FIG. 11, the total food intake was the highest in Example 2 throughout the test period, and a significant difference was observed between Reference Example 1 and Example 1. Furthermore, a total calorie intake was the lowest in Example 1 throughout the test period, and a significant difference was observed between Reference Example 1 and Example 2.

(Body Weight)

Figure 12:
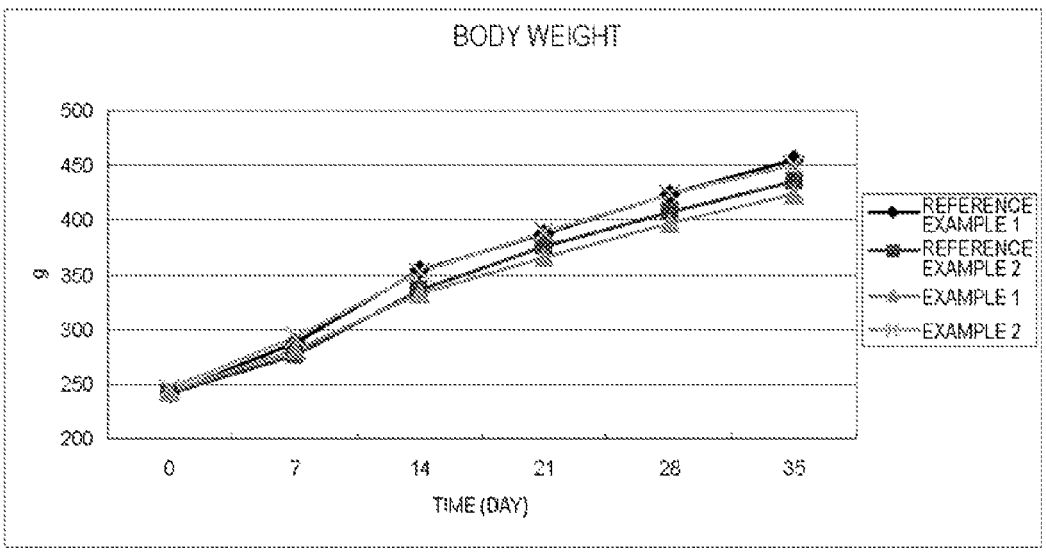
FIG. 12 A view showing the body weight during a test period in examples.

FIG. 12 is a view showing the trend of body weight during a test period. During the test period, each of the rats grew well without showing abnormality. As shown in FIG. 12, the body weight tended to become the lowest in Example 1 throughout the test period. Moreover, on the 14th day of test period, a significant difference was observed between Example 1 as well as Reference Example 2 and Reference Example 1.

The present application claims priority based on Japanese Patent Application No. 2012-100657 filed on Apr. 26, 2012, and the entire content of which is incorporated herein.

The invention claimed is:

1. An intestinal environment-improving agent comprising, as an effective component, a starch with a high resistant starch content that satisfies the following conditions (a), (b), (c), and (d):
   (a) a content of a resistant starch measured by the resistant starch measurement method of AOAC official method 2002. 02 is equal to or higher than 60%;
   (b) a peak molecular weight measured using HPLC unit with a calibration curve prepared using pullulan is equal to or higher than $6 \times 10^3$ and equal to or lower than $4 \times 10^4$;
   (c) a molecular weight dispersity is equal to or higher than 1.5 and equal to or lower than 6.0; and
   (d) a gelatinization enthalpy at 50° C. to 130° C. measured by a differential scanning calorimetry is equal to or lower than 10 J/g.

2. The intestinal environment-improving agent according to claim 1, wherein the starch with a high resistant starch content is obtainable by using a starch with a high amylose content that has an amylose content of equal to or higher than 40% as a raw material and treating the raw material with an acid in an aqueous inorganic acid solution.

3. The intestinal environment-improving agent according to claim 1 that has a function of increasing the number of enteric bacteria belonging to the genus *Bifidobacterium*.

4. The intestinal environment-improving agent according to claim 1 that has a lipid metabolism-improving function.

5. The intestinal environment-improving agent according to claim 4,
   wherein the lipid metabolism-improving function is a function of decreasing a total cholesterol level in blood.

6. The intestinal environment-improving agent according to claim 4,
   wherein the lipid metabolism-improving function is a function of decreasing levels of triglyceride in blood.

7. The intestinal environment-improving agent according to claim 4,
   wherein the lipid metabolism-improving function is a function of decreasing an arteriosclerotic index represented by the following Formula (I):

$$\text{arteriosclerotic index} = ((\text{total cholesterol concentration (mg/dl)}) - (\text{HDL cholesterol concentration (mg/dl)}))/(\text{HDL cholesterol concentration (mg/dl)}) \quad (I).$$

8. The intestinal environment-improving agent according to claim 4, further comprising an insoluble dietary fiber.

9. The intestinal environment-improving agent according to claim 8,
   wherein the insoluble dietary fiber is a cellulose or a cellulose derivative.

10. The intestinal environment-improving agent according to claim 9,
    wherein the insoluble dietary fiber is cellulose.

11. Drink or food comprising the intestinal environment-improving agent according to claim 1.

12. A feed comprising the intestinal environment-improving agent according to claim 1.

* * * * *